US007005448B2

(12) United States Patent
May

(10) Patent No.: US 7,005,448 B2
(45) Date of Patent: Feb. 28, 2006

(54) AMINOALKYL-BENZOFURAN-5-OL COMPOUNDS FOR THE TREATMENT OF GLAUCOMA

(75) Inventor: Jesse A. May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 64 days.

(21) Appl. No.: 10/498,835

(22) PCT Filed: Dec. 5, 2002

(86) PCT No.: PCT/US02/38908

§ 371 (c)(1),
(2), (4) Date: Jun. 14, 2004

(87) PCT Pub. No.: WO03/051352

PCT Pub. Date: Jun. 26, 2003

(65) Prior Publication Data

US 2004/0259941 A1 Dec. 23, 2004

Related U.S. Application Data

(60) Provisional application No. 60/340,361, filed on Dec. 14, 2001.

(51) Int. Cl.
*A61K 31/343* (2006.01)
*C07D 405/02* (2006.01)
*C07D 405/06* (2006.01)
*C07D 307/78* (2006.01)
*C07D 307/87* (2006.01)

(52) U.S. Cl. .................... 514/469; 549/462; 549/469
(58) Field of Classification Search ............. 549/462, 549/469; 514/469; 548/517
See application file for complete search history.

(56) References Cited

U.S. PATENT DOCUMENTS

| 5,011,846 | A | 4/1991 | Gittos et al. |
| 5,106,555 | A | 4/1992 | Kobayashi et al. |
| 5,290,781 | A | 3/1994 | Espino et al. |
| 5,538,974 | A | 7/1996 | Ogawa et al. |
| 5,652,272 | A | 7/1997 | Ogawa et al. |
| 5,693,654 | A | 12/1997 | Birch |
| 2003/0092774 | A1 | 5/2003 | Parkinson et al. |

FOREIGN PATENT DOCUMENTS

| EP | 0 522 226 B1 | 9/1997 |
| EP | 0 771 563 B1 | 1/2003 |
| WO | WO 92/20333 A1 | 11/1992 |
| WO | WO 97/17345 | 5/1997 |
| WO | WO 00/44737 A1 | 8/2000 |

OTHER PUBLICATIONS

Ahmad, "Fluoxetine and Glaucoma," *Annals of Pharmacotherapy*, 25:436 (1991).

Barnett et al., "The Presence of Serotonin (5-$HT_1$) Receptors Negatively Coupled to Adenylate Cyclase in Rabbit and Human Iris-Ciliary Processes," *Exp. Eye Res.*, 57:209-216 (1993).

Chang et al., "Mechanism of the Ocular Hypotensive Action of Ketanserin," *J. of Ocular Pharmacology*, 1(2):137-147 (1985).

Chidlow et al., "Characteristics of [$^3$H]5-Hydroxytryptamine Binding to Iris-Ciliary Body Tissue of the Rabbit," *Invest. Ophthal. & Vis. Sci.*, 36(11):2238-2245 (1995).

Costagliola et al., "Effect of Oral Ketanserin Administration on Intraocular Pressure in Glaucomatous Patients," *Exp. Eye Res.* 52:507-510 (1991).

Costagliola et al., "Fluoxetine and Administration Increases Intraocular Pressure," *Brt. J. Ophthalmol*, 80:678 (1996).

Eglen et al., "The 5-$HT_7$ Receptor: Orphan Found," *Trends Pharmacol. Sci,*, 18:104-7 (1997).

Heidmann et al., "Four 5-Hydroxytryptamine$_7$ (5-$HT_7$) Receptor Isoforms in Human and Rat Produced by Alternative Splicing: Species Differences Due to Altered Intron—Exon Organization," *J. of Neurochemistry*, 68(4): 1372-1381 (1997).

Hoyer et al., "VII. International Union of Pharmacology Classification of Receptors for 5-Hydroxytryptamine (Serotonin)," *Pharmacological Reviews*, 46(2):157-203 (1994 ).

Krootila et al., "Effect of Serotonin and Its Antagonist (Ketanserin) on Intraocular Pressure in the Rabbit," *J. of Ocular Pharmacology*, 3(4):279-290 (1987).

Mallorga et al., "Characterization of Serotonin Receptors in the Iris + Ciliary Body of the Albino Rabbit," *Current Eye Research* 6(3):527-532 (1987).

Mano et al., "The Effect of ANPLAG® (Sarpogrelate HCL), New Selective 5-$HT_2$ Antagonist on Intraocular Pressure in Glaucoma Patients," *Invest. Orphthal. & Vis. Sci.*, 36(4): 3322-309 (S719) (1995).

Martin et al., "The Structure and Signalling Properties of 5-HT Receptors: An Endless Diversity?", *Trends Pharmacol. Sci.*, 19:2-4 (1998).

Martin et al., "Serotonin in Human Aqueous Humor," *Ophthalmol*, 95(9):1221-1226 (1998).

Meyer-Bothling et al., "Topical Application of Serotonin or the 5-$HT_1$-Agonist 5-CT Intraocular Pressure in Rabbits," *Invest. Ophthal. & Vis. Sci.*, 34(10):3035-3042 (1993).

Osborne et al., "Do Beta-Adrenoceptors and Serotonin 5-$HT_{1A}$ Receptors Have Similar Functions in the Control of Intraocular Pressure in the Rabbit," *Ophthalmologica* 210: 308-314 (1996).

(Continued)

Primary Examiner—Rita Desai
(74) Attorney, Agent, or Firm—Patrick M. Ryan

(57) ABSTRACT

The present invention provides novel compounds, compositions containing the compounds of the invention in a pharmaceutically acceptable excipient and methods for using the compositions for lowering intraocular pressure.

17 Claims, No Drawings

OTHER PUBLICATIONS

Takenaka et al, "The Effect of ANPLAG® (Sarpogrelate HCL), Novel Selective 5-$HT_2$ Antagonist on Intraocular Pressure in Glaucoma Patients," *Invest. Ophthal. & Vis. Sci.*, 36(4):3390-377 (1995).

Tobin et al., "Evidence for the Presence of Serotonin Receptors Negatively Coupled to Adenylate Cyclase in the Rabbit Iris-Ciliary Body," *J. of Neurochemistry*, 53(3):686-691 (1989).

Tobin et al., "Evidence for the Presence of Serotonergic Nerves and Receptors in the Iris-Ciliary Body Complex of the Rabbit," *J. of Neuroscience*, 8(10):3713-3721 (1988).

Wang et al., "Effect of 5-methylurapidil, an $\alpha_{1a}$-adrenergic Antagonist and 5-hydroxytryptamine$_{1a}$ Agonist, on Aqueous Humor Dynamics in Monkeys and Rabbits," *Current Eye Research*, pp. 769-775 (Apr. 1997).

Wang et al., "Effect of p-MPPI Hydrochloride (p-MPPI) Applied Before 5-Methylurapidil (5-MU) on Intraocular Pressure (IOP) in Normal Monkeys," *Invest. Ophthal. & Vis. Sci.*, 39(4):2236-B93 (S488) (1998).

Zifa et al., "5-Hydroxytryptamine Receptors," *Pharmaceutical Reviews*, 44(3):401-548):1992.

Parker et al., "A Novel (Benzodifuranyl)aminoalkane with Extremely Potent Activity at the 5-$HT_{2A}$ Receptor," *J. Med. Chem.*, vol. 41, pp. 5148-5149 (1998).

English Abstract AN 1984:68106, RN#88745-48-6-P, 88745-49-7P, 88745-50-0, 88745-51-1P (Database CAPLUS on STN).

AMINOALKYL-BENZOFURAN-5-OL COMPOUNDS FOR THE TREATMENT OF GLAUCOMA

This application claims benefit of Provisional Application Ser. No. 60/340,361, filed Dec. 14, 2001.

BACKGROUND OF THE INVENTION

1. Field of the Invention

The present invention relates to treatment for lowering intraocular pressure and to compounds for use in such treatments. More particularly, the present invention relates to the use of compounds with serotonergic 5-HT5-HT$_2$ agonist activity to lower intraocular pressure (IOP), treat glaucoma, and to provide neuroprotection.

2. Description of the Related Art

Serotonin (5-hydroxy tryptamine; 5-HT5-HT) is an endogenous biogenic amine with a well defined neurotransmitter function in many tissues of the body including the eye [Zifa and Fillion 1992; Hoyer et al. 1994; Tobin et al. 1988].

5-HT is known to interact with at least seven major 5-HT receptors (5-HT$_1$–5-HT$_7$) and additional subtypes within these families to initiate intracellular biochemical events such as stimulation of second messengers (e.g. cAMP, inositol trisphosphate) eventually leading to the final biological response, for example, tissue contraction or hormone release, etc. [Hoyer et al. 1994; Martin et al. 1998]. Receptor subtypes within the 5-HT$_1$ family are negatively coupled to adenylyl cyclase (AC) and cause inhibition of cAMP production, while 5-HT$_4$, 5-HT$_6$, and 5-HT$_7$ receptors are positively coupled to AC and thus stimulate cAMP production when activated by 5-HT [Martin et al. 1998]. The receptors in the 5-HT$_2$ family are positively coupled to phospholipase C (PLC) and thus generate inositol phosphates and mobilize intracellular calcium when activated to mediate the effects of 5-HT. The 5-HT$_3$ receptor is unique in that it couples to an ion channel which gates sodium, potassium, and calcium [Hoyer et al. 1994].

The human and animal 5-HT$_7$ receptor has only recently been cloned, expressed, and shown to be present in various brain areas and peripheral tissues [Eglen et al. 1997]. Recent studies have shown there to be four splice variants of the 5-HT$_7$ receptor [Heidmann et al. 1997]. It has been proposed that the 5-HT$_7$ receptor may be involved in the pathophysiology of sleep disorders, depression, and other psychiatric disorders [Eglen et al. 1997]. In the periphery, stimulation of 5-HT$_7$ receptors results in relaxation of blood vessels and hence vasodilation [Eglen et al. 1997].

Known compounds exhibiting 5-HT$_2$ agonist activity have typically been designed to treat numerous central nervous system (CNS)-related conditions, particularly the treatment of obesity and depression, by activation of 5-HT$_{2C}$ receptors. Thus, one desired property of known 5-HT$_2$ agonist compounds is that they easily penetrate the blood brain barrier. Compounds possessing the property of penetration into the CNS generally do not contain polar groups.

To treat ocular diseases, it is desirable to administer compositions orally or topically that will remain in the ocular tissues and not cross the blood brain barrier to enter the CNS. What are needed are 5-HT$_2$ agonist compounds that are useful in the treatment of ocular diseases characterized by an elevated intraocular pressure, the treatment of glaucoma and neuroprotection. Such compounds would not have a propensity to cross the blood brain barrier.

SUMMARY OF THE INVENTION

The present invention overcomes these and other drawbacks of the prior art by providing compounds having 5-HT$_2$ agonist activity that do not cross the blood brain barrier. More specifically, the present invention provides compounds having the following general formula:

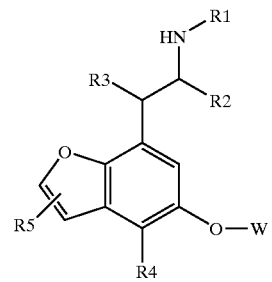

wherein $R^1$ is hydrogen or $C_{1-4}$alkyl; $R^2$ is hydrogen, $C_{1-4}$alkyl, or $R^1$ and $R^2$ can together be $(CH_2)_{2-4}$ to complete a heterocyclic ring; $R^3$ is hydrogen, hydroxyl, $C_{1-4}$alkoxy, or fluorine; $R^4$ is selected from $C_{1-4}$alkyl, halogen, nitrile, $C_{1-6}$alkylthio, trifluoromethyl, $C_{1-4}$alkyl substituted by HO or $C_{1-3}$alkoxy, $R^5$ is hydrogen, halogen, $C_{1-4}$alkoxy, nitrile, W is hydrogen or $C(=O)C_{1-8}$alkyl. In preferred embodiments, $R^1$, $R^3$ and $R^5$ are hydrogen, $R^2$ is methyl, $R^4$ is halogen, methyl or trifluoromethyl, and W is hydrogen. Most preferably, the compounds of the invention have an R-configuration at the carbon atom bearing the primary amine.

In another aspect, the present invention provides compositions containing the compounds described above in a pharmaceutically acceptable excipient. The compositions are most preferably in the form of topical ophthalmic formulations for delivery to the eye. The compounds of the invention may be combined with ophthalmologically acceptable preservatives, surfactants, viscosity enhancers, penetration enhancers, buffers, sodium chloride, and water to form an aqueous, sterile ophthalmic suspension or solution to form the compositions of the invention.

The compositions of the invention are preferably formulated as topical ophthalmic suspensions or solutions, with a pH of about 5 to 8. The compounds of the invention as described above will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the routine discretion of a skilled clinician.

The present invention further provides a method of lowering intraocular pressure in a mammal by administering to a patient in need thereof a therapeutically effective amount of a composition comprising a compound having the structure as described above in a pharmaceutically acceptable excipient. In preferred embodiments, the composition can be administered systemically or locally to the eye (e.g., topically, intracamerally, or via an implant).

DETAILED DESCRIPTION PREFERRED EMBODIMENTS

It has been found that serotonergic compounds which possess agonist activity at 5-HT$_2$ receptors effectively lower and control elevated IOP and glaucoma. Serotonergic nerves innervate the eye [Tobin et al. 1988] and 5-HT has been found in the aqueous humor of human eyes [Martin et al. 1988]. In addition, receptor binding sites for [$^3$H]5-HT have been demonstrated and pharmacologically characterized in the iris-ciliary body (ICB) of rabbits [Mallorga and Sugrue 1987; Chidlow et al. 1995]. These 5-HT binding sites have been shown to be functionally coupled to second messenger generation in rabbits [Tobin and Osborne 1989; Tobin et al. 1988]. In the human ICB these binding sites are characterized as 5-HT$_{1A}$ and 5-HT$_2$ receptors [Barnet and Osborne 1993]. In addition, the presence of mRNAs for 5-HT$_{1A}$ and 5-HT$_7$ receptors in the rabbit ICB have been reported [Chidlow et al. 1995; Osborne and Chidlow 1996]. The precise functions of these receptors in the eye are unknown, especially the 5-HT$_7$ subtype(s).

5-HT or 5-carboxamidotryptainine (5-CT) topically applied to the rabbit eye raise intraocular pressure in the anterior chamber of the eye [Meyer-Bothling et al. 1993]. By contrast, it has been shown that topically applied 5-HT lowers IOP [Krootila et al. 1987 (intracamerally 5-HT raised IOP and caused breakdown of the blood-aqueous barrier)]. In addition, the 5-HT uptake inhibitor, fluoxetine (Prozac®), also raises IOP in human subjects upon oral administration [Costagliola et al. 1996] and may cause glaucoma [Ahmad 1992]. However, the 5-HT receptor subtype(s) involved in the IOP-elevating effects of 5-HT, 5-CT and fluoxetine are unknown.

Studies conducted in rabbits with 8-hydroxy DPAT and MKC-242 (5-HT$_{1A}$ agonists) have shown these compounds lower IOP [Osborne and Chidlow 1996; EP 0771563-A2]. In addition, 5-methylurapidil (5-HT$_{1A}$ agonist) lowered IOP in glaucomatous monkeys [Wang et al. 1997]. Both MKC-242 and 5-methylurapidil are relatively potent α1 receptor antagonists (α1 antagonists are known to lower IOP in rabbits, monkeys, and man). The mechanism of action for lowering IOP by 5-methylurapidil has been attributed to its α1 antagonist activity and not its 5-HT$_{1A}$ agonist activity [Wang et al. 1998]. U.S. Pat. No. 5,693,654, discloses 5-HT$_1$ receptor agonists for lowering IOP. WO 92/20333 discloses certain 5-HT$_{1A}$ agonists for the treatment of glaucoma.

Methysergide (5-HT$_2$ antagonist) lowered IOP in rabbits [Krootila et al. 1987]. Ketanserin (5-HT$_{2A/C}$ antagonist), also with significant α1 antagonist activity, lowers IOP in rabbits and man [Chan et al. 1985; Costagliola et al. 1991]. Saprogrelate (5-HT$_{2A}$ antagonist) lowers IOP in rabbits and in man when dosed topically or orally [Mano et al. 1995; Takenaka et al. 1995]. EP 522226 and U.S. Pat. No. 5,290, 781 disclose the use of ketanserin and its derivatives for treating ocular hypertension. U.S. Pat. Nos. 5,290,781 and 5,106,555 discloses the use of certain 5-HT$_2$ antagonists for lowering, IOP. U.S. Pat. No. 5,652,272 discloses saprogrelate for reducing IOP. U.S. Pat. No. 5,538,974 discloses opthalmic compositions of certain 5-HT$_2$ antagonists for lowering IOP.

U.S. Pat. No. 5,011,846 discloses certain 5-HT$_3$ receptor antagonists for treating glaucoma.

WO 97/17345 discloses that particular compounds with 5-HT$_4$ serotonergic receptor agonist or antagonist activity are useful for treating psychiatric, gastrointestinal, lower urinary, and cardiovascular disorders. The publication mentions the compounds may also be useful for glaucoma.

The present inventor has discovered that compounds with the general formula (I) have 5-HT$_2$ agonist activity and may be useful in lowering IOP, treating glaucoma, and/or provide neuroprotection for retinal ganglion cells.

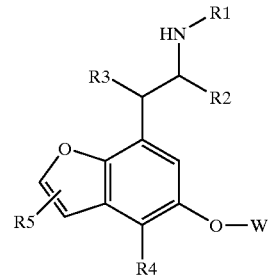

Formula (I)

In Formula I, $R^1$ is hydrogen or $C_{1-4}$ alkyl; $R^2$ is hydrogen, $C_{1-4}$alkyl, or $R^1$ and $R^2$ together can be $(CH_2)_{2-4}$ to complete a heterocyclic ring; $R^3$ is hydrogen, hydroxyl, $C_{1-4}$alkoxy, or fluorine; $R^4$ is selected from $C_{1-4}$alkyl, halogen, nitrile, $C_{1-6}$alkylthiol, trifluoromethyl, $C_{1-4}$alkyl substituted by HO or $C_{1-3}$alkoxy, $R^5$ is hydrogen, halogen, $C_{1-4}$alkoxy, nitrile and W is hydrogen or C(=O)$C_{1-8}$alkyl.

The compounds of the invention will preferably possess the following properties: 1) agonist acitivty at the 5-HT$_2$ receptors, and 2) significantly greater chemical stability than serotonin, the endogenous receptor ligand.

D. E. Nichols and colleagues at Purdue University have developed a number of benzofuran- and benzodifuranyl-alkylamines over the past decade and have demonstrated their affinity and efficacy at the 5-HT$_{2A}$ receptor as well as their hallucinogenic activity as evaluated in animals. Dr. Nichols' focus has been on the development of compounds with CNS activity, that is, that readily cross the blood brain barrier. Thus, these known compounds are outside of the scope of the compounds encompassed by Formula I above.

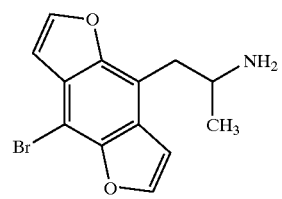

For example, Nichols has developed a compound with the following structure (compound 1) (Parker et al. 1998).

Compound I

The Nichols compound has been shown to have a high affinity for the 5-HT$_{2A}$ receptor and to generalize to LSD in drug discrimination studies. Nichols and colleagues also studied compounds in the class of that shown below (compound 2) for CNS activity.

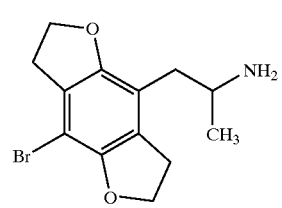

Compound 2

(Monte et al. 1996). Neither of the compounds studied by Nichols and colleagues is within the scope of the present invention. Furthermore, Nichols does not discuss use of compounds 1 or 2 for the treatment of any ocular diseases, ocular hypertension or glaucoma. The goal in creating compounds 1 and 2 was to produce compounds useful for CNS disorders and such compounds would necessarily have to have the ability to penetrate the blood brain barrier. In contrast, the compounds of the present invention are designed not to cross the blood brain barrier but to remain in the ocular tissue.

Eli Lilly developed a series of benzofuran compounds that are similar to the compounds of Formula I herein. (WO 00/44737). Lilly's compounds have the following general formula:

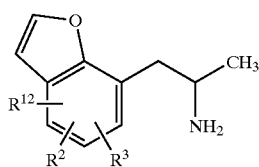

These compounds are described as having utility for numerous CNS-related conditions, particularly the treatment of obesity and depression by activation of 5-$HT_{2C}$ receptors. Thus, it is desirable that these compounds would penetrate into the brain. None of the compounds described in Lilly come within scope of the present invention. The compounds of the invention are designed to avoid penetration into the brain whereas the Lilly compounds are specifically aimed at crossing the blood brain barrier in order to treat CNS diseases.

The compounds of the invention have a low propensity to enter the CNS, or to cross the blood brain barrier, due to the presence of the highly polar hydroxyl group. Thus, the compounds of the invention are less likely to elicit undesirable centrally mediated side effects, such as those associated with the CNS active compounds described by Nichols and Lilly. The preferred 4-substituted 7-(2-aminopropyl)-benzofuran-5-ol compounds of Formula I have a greater chemical stability than serotonin or other indole analogs.

The compounds of the invention may be prepared by known synthetic procedures, such as those reported in WO 00/44737, and other well known synthetic transformations.

The compounds of the invention can be administered systemically or locally to the eye (e.g., topically, intracamerally, or via an implant). The compounds are preferrably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable is surfactant to assist in dissolving the compound. Additionally, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

The compounds of the invention are preferably formulated as topical ophthalmic suspensions or solutions, with a pH of about 5 to 8. The compounds will normally be contained in these formulations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the routine discretion of a skilled clinician.

The compounds can also be used in combination with other IOP lowering agents, such as, but not limited to, β-blockers, prostaglandins, carbonic anhydrase inhibitors, area $\alpha_{-2}$ agonists and miotics. The compounds can also be used in combination with other agents useful for treating glaucoma, such as, but not limited to, calcium channel blockers and NMDA antagonists. These agents may be administered topically, but usually systemically.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. Nos. 5,011,846 5,106,555 5,290,781 5,538,974 5,652,272 5,693,654

Foreign Patents and Published Applications

EP 0771563-A2

EP 522226

WO 92/20333

WO 97/17345

Other Publications

Ahmad, *Ann. Pharmacother.*, 25:436, 1992.

Barnet and Osborne, *Exp. Eye Res.*, 57:209–216, 1993.

Chan et al., *J. Ocular Pharmacol.*, 1:137–147, 1985.

Chidlow et al., *Invest. Ophthalmol. Vis. Sci.*, 36:2238–2245, 1995.

Costagliola et al., *Br. J. Ophthalmol.*, 80:678, 1996.

Costagliola et al., *Ex. Eye Res.*, 52:507–510, 1991.

Eglen et al., *Trend Pharmacol. Sci.*, 18:104–107, 1997.

Heidmann et al., *J. Neurochem.*, 68:1372–1381, 1997.

Hoyer et al., *Pharmacol. Rev.*, 46:157–203, 1994.

Krootila et al., *J. Ocular Pharmacol.*, 3:279–290, 1987.

Mallorga and Sugrue, *Curr. Eye Res.*, 6:527–532, 1987.

Mano et al., *Invest. Ophthal. Vis. Sci.*, 36(Suppl):3322–309, 1995.

Martin et al., *Ophthalmol.*, 95:1221–1226, 1988.

Martin et al., *Trends Pharmacol. Sci.*, 19:2–4, 1998.

Meyer-Bothling et al., *Invest. Ophthalmol. Vis. Sci.*, 34:3035–3042, 1993.

Osborne and Chidlow, *Ophthalmologica*, 210:308–314, 1996.

Takenaka et al., *Invest Ophthal. Vis. Sci.*, 36(Suppl): 3390–377, 1995.

Tobin et al., *J. Neurosci.*, 8:3713–3721, 1988.

Tobin and Osborne, *J. Neurochem.*, 53:686–601, 1989.

Wang et al., *Curr. Eye Res.*, 16:679–775, 1997.

Wang et al., *Invest. Ophthal. Vis. Sci.*, 39(Suppl):2236–488, 1998.

Zifa and Fillion, *Pharmacol. Rev.*, 44:401–458, 1992.

What is claimed is:

1. A compound having the structure as follows:

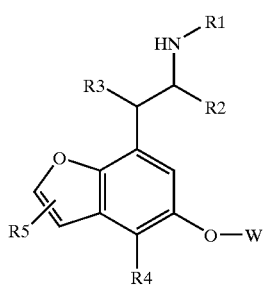

wherein $R^1$ is hydrogen or $C_{1-4}$alkyl; $R^2$ is hydrogen, $C_{1-4}$alkyl, or $R^1$ and $R^2$ can together be $(CH_2)_{2-4}$ to complete a heterocyclic ring; $R^3$ is hydrogen, hydroxyl, $C_{1-4}$alkoxy, or fluorine; $R^4$ is selected from $C_{1-4}$alkyl, halogen, nitrile, $C_{1-6}$alkylthiol, trifluoromethyl, $C_{1-4}$alkyl substituted by HO or $C_{1-3}$alkoxy, $R^5$ is hydrogen, halogen, $C_{1-4}$alkoxy, nitrile, W is hydrogen or $C(=O)C_{1-8}$alkyl.

2. The compound of claim 1, wherein $R^1$, $R^3$ and $R^5$ are hydrogen, $R^2$ is methyl, $R^4$ is halogen, methyl or trifluoromethyl, $C_{1-4}$alkyl substituted by HO or $C_{1-3}$alkoxy, and W is hydrogen.

3. The compound of claim 2, further defined as the stereoisomer with an R-configuration at the carbon atom bearing the primary amine.

4. A composition comprising at least one compound having the structure as follows and a pharmaceutically acceptable excipient:

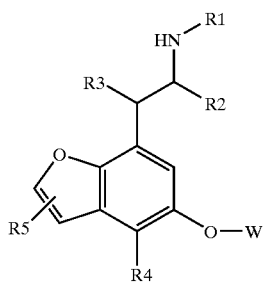

wherein $R^1$ is hydrogen or $C_{1-4}$alkyl; $R^2$ is hydrogen, $C_{1-4}$alkyl, or $R^1$ and $R^2$ can together be $(CH_2)_{2-4}$ to complete a heterocyclic ring; $R^3$ is hydrogen, hydroxyl, $C_{1-4}$alkylthiol, or fluorine; $R^4$ is selected from $C_{1-4}$alkyl, halogen, nitrile, $C_{1-6}$alkylthiol, trifluoromethyl, $C_{1-4}$alkyl substituted by HO or $C_{1-3}$alkoxy, $R^5$ is hydrogen, halogen, $C_{1-4}$alkoxy, nitrile, W is hydrogen or $C(=O)C_{1-8}$alkyl.

5. The composition of claim 4, wherein the compound is further defined as follows: $R^1$, $R^3$ and $R^5$ are hydrogen, $R^2$ is methyl, $R^4$ is halogen, methyl or trifluoromethyl, $C_{1-4}$alkyl substituted by HO or $C_{1-3}$alkoxy, and W is hydrogen.

6. The composition of claim 5, wherein the compound is further defined as the stereoisomer with an R-configuration at the carbon atom bearing the primary amine.

7. The composition of claim 4, further comprising an ophthalmologically acceptable preservative.

8. The composition of claim 4, further comprising an ophthalmologically acceptable surfactant.

9. The composition of claim 4, further comprising an agent selected from the group consisting of hydroxymethylcellulose, hydroxyethylcellulose, hydroxypropylmethylcellulose, methylcellulose, and polyvinylpyrrolidone.

10. The composition of claim 4, further defined as a topical ophthalmic suspension or solution having a pH of about 5 to about 8.

11. The composition of claim 10, wherein the concentration of the compound is from 0.01% to 5% by weight.

12. The composition of claim 11, wherein the composition of the compound is from 0.25% to 2% by weight.

13. A method of lowering intraocular pressure in a mammal, said method comprising administering to a patient in need thereof a therapeutically effective amount of a composition comprising a compound having the structure as follows:

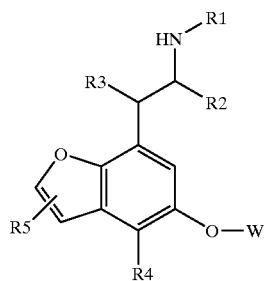

wherein $R^1$ is hydrogen or $C_{1-4}$alkyl; $R^2$ is hydrogen, $C_{1-4}$alkyl, or $R^1$ and $R^2$ can together be $(CH_2)_{2-4}$ to complete a heterocyclic ring; $R^3$ is hydrogen, hydroxyl, $C_{1-4}$alkoxy, or fluorine; $R^4$ is selected from $C_{1-4}$alkyl, halogen, nitrile, $C_{1-6}$alkylthiol, trifluoromethyl, $C_{1-4}$alkyl substituted by HO or $C_{1-3}$alkoxy, $R^5$ is hydrogen, halogen, $C_{1-4}$alkoxy, nitrile, W is hydrogen or $C(=O)C_{1-8}$alkyl.

14. The method of claim 13, wherein $R^1$, $R^3$ and $R^5$ are hydrogen, $R^2$ is methyl, $R^4$ is halogen, methyl or trifluoromethyl, $C_{1-4}$alkyl substituted by HO or $C_{1-3}$alkoxy, and W is hydrogen.

15. The method of claim 14, wherein the compound is further defined as the diastereomer with an R-configuration at the carbon atom bearing the primary amine.

16. The method of claim 13, wherein the composition is in the form of a topical ophthalmic suspension or solution.

17. The method of claim 13, wherein the composition is administered by topical application to the eye.

* * * * *